United States Patent
Wong Po Foo et al.

(10) Patent No.: US 11,357,463 B2
(45) Date of Patent: Jun. 14, 2022

(54) TARGET SITE SELECTION, ENTRY AND UPDATE WITH AUTOMATIC REMOTE IMAGE ANNOTATION

(71) Applicant: BioCardia, Inc., San Carlos, CA (US)

(72) Inventors: Cheryl Wong Po Foo, Santa Clara, CA (US); David Sanderson, Burlingame, CA (US); Peter Altman, Menlo Park, CA (US)

(73) Assignee: BIOCARDIA, INC., San Carlos, CA (US)

( * ) Notice: Subject to any disclaimer, the term of this patent is extended or adjusted under 35 U.S.C. 154(b) by 166 days.

(21) Appl. No.: 14/793,594

(22) PCT Filed: Jan. 8, 2014

(86) PCT No.: PCT/US2014/010732
§ 371 (c)(1),
(2) Date: Jul. 7, 2015

(87) PCT Pub. No.: WO2014/110169
PCT Pub. Date: Jul. 17, 2014

(65) Prior Publication Data
US 2016/0000392 A1    Jan. 7, 2016

Related U.S. Application Data

(60) Provisional application No. 61/750,226, filed on Jan. 8, 2013, provisional application No. 61/750,233, filed (Continued)

(51) Int. Cl.
*A61B 6/00* (2006.01)
*A61B 6/12* (2006.01)
(Continued)

(52) U.S. Cl.
CPC ............ *A61B 6/468* (2013.01); *A61B 5/0035* (2013.01); *A61B 5/0044* (2013.01); *A61B 5/055* (2013.01);
(Continued)

(58) Field of Classification Search
CPC ... A61B 2034/00; A61B 2090/00; A61B 5/00; A61B 6/00; A61B 8/00; A61B 6/468;
(Continued)

(56) References Cited

U.S. PATENT DOCUMENTS 5,892,509 A * 4/1999 Jakobs .................... G06F 1/189
345/173
6,368,285 B1 * 4/2002 Osadchy .............. A61B 5/0064
600/508

(Continued)

FOREIGN PATENT DOCUMENTS

JP    2001149382 A    6/2001
JP    2005013358 A    1/2005

(Continued)

OTHER PUBLICATIONS

Sterile field, (n.d.) Mosby's Medical Dictionary, 9th edition. (2009). Retrieved May 25, 2018 from https://medical-dictionary.thefreedictionary.com/sterile+field.*

(Continued)

*Primary Examiner* — Sean D Mattson
(74) *Attorney, Agent, or Firm* — Wilson Sonsini Goodrich & Rosati

(57) ABSTRACT

Fluoroscopic imaging of a patient's heart is performed by positioning a patient in a sterile field and imaging the heart using a x-ray fluoroscopy system within the sterile to produce a two-dimensional image. The two-dimensional image is simultaneously displayed on an operative display within or adjacent the sterile filed and on a display of a (Continued)

remote image processor outside the operative field. The two-dimensional image of the remote display is manually marked or annotated to show anatomical or treatment information which is simultaneously shown on the operative display.

21 Claims, 8 Drawing Sheets

Related U.S. Application Data on Jan. 8, 2013, provisional application No. 61/750,237, filed on Jan. 8, 2013.

(51) Int. Cl.
*A61B 5/00* (2006.01)
*A61B 8/08* (2006.01)
*A61B 5/055* (2006.01)
*A61B 6/03* (2006.01)
*A61B 90/00* (2016.01)
*A61B 34/20* (2016.01)

(52) U.S. Cl.
CPC ............... *A61B 6/032* (2013.01); *A61B 6/12* (2013.01); *A61B 6/463* (2013.01); *A61B 6/464* (2013.01); *A61B 6/466* (2013.01); *A61B 6/481* (2013.01); *A61B 6/485* (2013.01); *A61B 6/487* (2013.01); *A61B 6/503* (2013.01); *A61B 6/5235* (2013.01); *A61B 6/5247* (2013.01); *A61B 8/0883* (2013.01); *A61B 8/0891* (2013.01); *A61B 2034/2065* (2016.02); *A61B 2090/374* (2016.02); *A61B 2090/376* (2016.02); *A61B 2090/378* (2016.02); *A61B 2090/3762* (2016.02)

(58) Field of Classification Search
CPC ......... A61B 6/464; A61B 6/463; A61B 6/503; A61B 6/485; A61B 6/5247; A61B 6/5235; A61B 6/487; A61B 6/481; A61B 6/466; A61B 6/12; A61B 6/032; A61B 8/0891; A61B 8/0883; A61B 5/0035; A61B 5/0044; A61B 5/055; A61B 2090/378; A61B 2090/3762; A61B 2090/374; A61B 2090/376; A61B 2034/2065
See application file for complete search history.

(56) References Cited

U.S. PATENT DOCUMENTS

| | | | |
|---|---|---|---|
| 6,466,813 B1 | 10/2002 | Shukla et al. | |
| 6,493,575 B1* | 12/2002 | Kesten | A61B 90/36 600/431 |
| 7,749,215 B1* | 7/2010 | Ben-Haim | A61M 25/0084 604/510 |
| 7,848,553 B2 | 12/2010 | Hertel et al. | |
| 2003/0083563 A1* | 5/2003 | Katsman | A61B 6/563 600/407 |
| 2004/0225328 A1 | 11/2004 | Okerlund et al. | |
| 2007/0016029 A1* | 1/2007 | Donaldson | A61B 5/7475 600/437 |
| 2007/0055142 A1* | 3/2007 | Webler | A61B 5/06 600/425 |
| 2007/0156017 A1* | 7/2007 | Lamprecht | A61B 1/00193 600/102 |
| 2008/0043901 A1 | 2/2008 | Maschke | |
| 2008/0139896 A1* | 6/2008 | Baumgart | G06F 3/04817 600/300 |
| 2008/0175455 A1* | 7/2008 | John | A61B 6/032 382/130 |
| 2008/0218588 A1* | 9/2008 | Stetten | A61B 8/587 348/47 |
| 2008/0262342 A1* | 10/2008 | Averbruch | A61B 6/12 600/424 |
| 2008/0283771 A1 | 11/2008 | Li | |
| 2009/0082660 A1* | 3/2009 | Rahn | A61B 6/12 600/411 |
| 2009/0088830 A1 | 4/2009 | Mohamed et al. | |
| 2009/0118609 A1* | 5/2009 | Rahn | A61B 6/12 606/34 |
| 2009/0282371 A1* | 11/2009 | Curl | G16H 40/20 715/863 |
| 2011/0021911 A1* | 1/2011 | Waters | A61B 8/0883 600/439 |
| 2011/0087088 A1 | 4/2011 | Korn et al. | |
| 2011/0087110 A1* | 4/2011 | Nathan | G06F 19/321 600/476 |
| 2011/0251483 A1* | 10/2011 | Razzaque | A61B 6/466 600/424 |
| 2012/0289825 A1 | 11/2012 | Rai et al. | |
| 2013/0102890 A1 | 4/2013 | Dib | |

FOREIGN PATENT DOCUMENTS

| | | |
|---|---|---|
| JP | 2012081202 A | 4/2012 |
| JP | 2012223500 A | 11/2012 |
| WO | WO-2009137688 A2 | 11/2009 |
| WO | WO-2014110169 A1 | 7/2014 |

OTHER PUBLICATIONS

Huang, Ngan F., et al. "Injectable biopolymers enhance angiogenesis after myocardial infarction." Tissue engineering11.11-12 (2005): 1860-1866. (Year: 2005).*

International search report and written opinion dated May 27, 2014 for PCT/US2014/010732.

Tomkowiak, et al. Targeted transendocardial therapeutic delivery guided by MRI-x-ray image fusion. Catheter Cardiovasc Interv. Sep. 1, 2011;78(3):468-78. doi: 10.1002/ccd.22901. Epub Mar. 16, 2011.

European Search Report and Search Opinion dated Aug. 18, 2016 for European Patent Application No. 14738045.5.

* cited by examiner

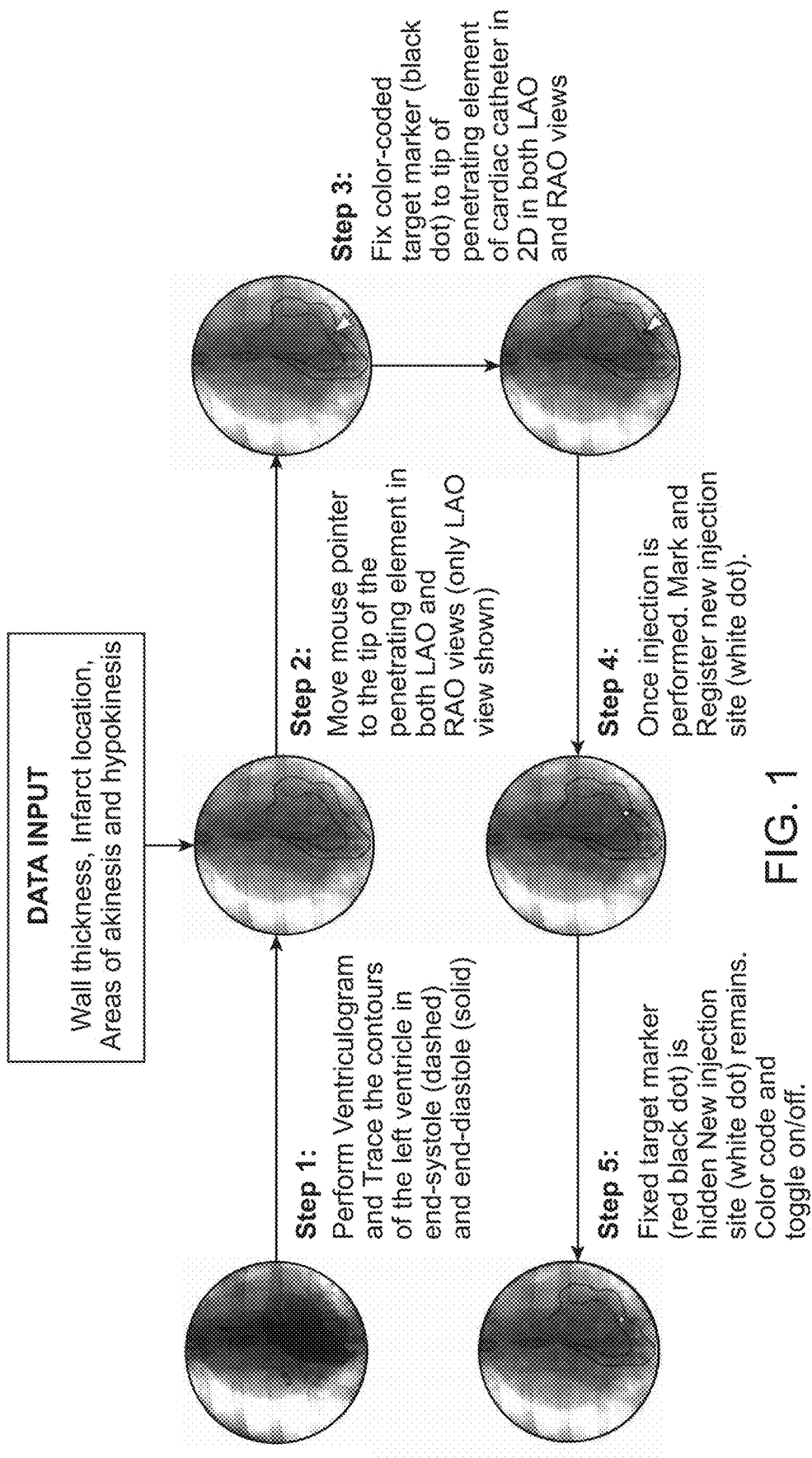

FIG. 1

Example 1. Recording of left ventricular contours and target sites on screen - 2D. Shown in one orthogonal view only. Recordings are done in both orthogonal view (other view not shown here) and the same procedure followed. Data Input from assessment of other imaging results such as MRI, CT, Echo, PET.

DATA INPUT
Wall thickness, Infarct location, Areas of akinesis and hypokinesis

Step 1:
Perform Ventriculogram and Trace the contours of the left ventricle in end-systole (dashed) and end-diastole (solid)

Step 2:
Move mouse pointer to the tip of the penetrating element in both LAO and RAO views (only LAO view shown)

Step 3:
Fix color-coded target marker (black dot) to tip of penetrating element of cardiac catheter in 2D in both LAO and RAO views Step 4:
Once injection is performed. Mark and Register new injection site (white dot).

Step 5:
Fixed target marker (red black dot) is hidden New injection site (white dot) remains. Color code and toggle on/off.

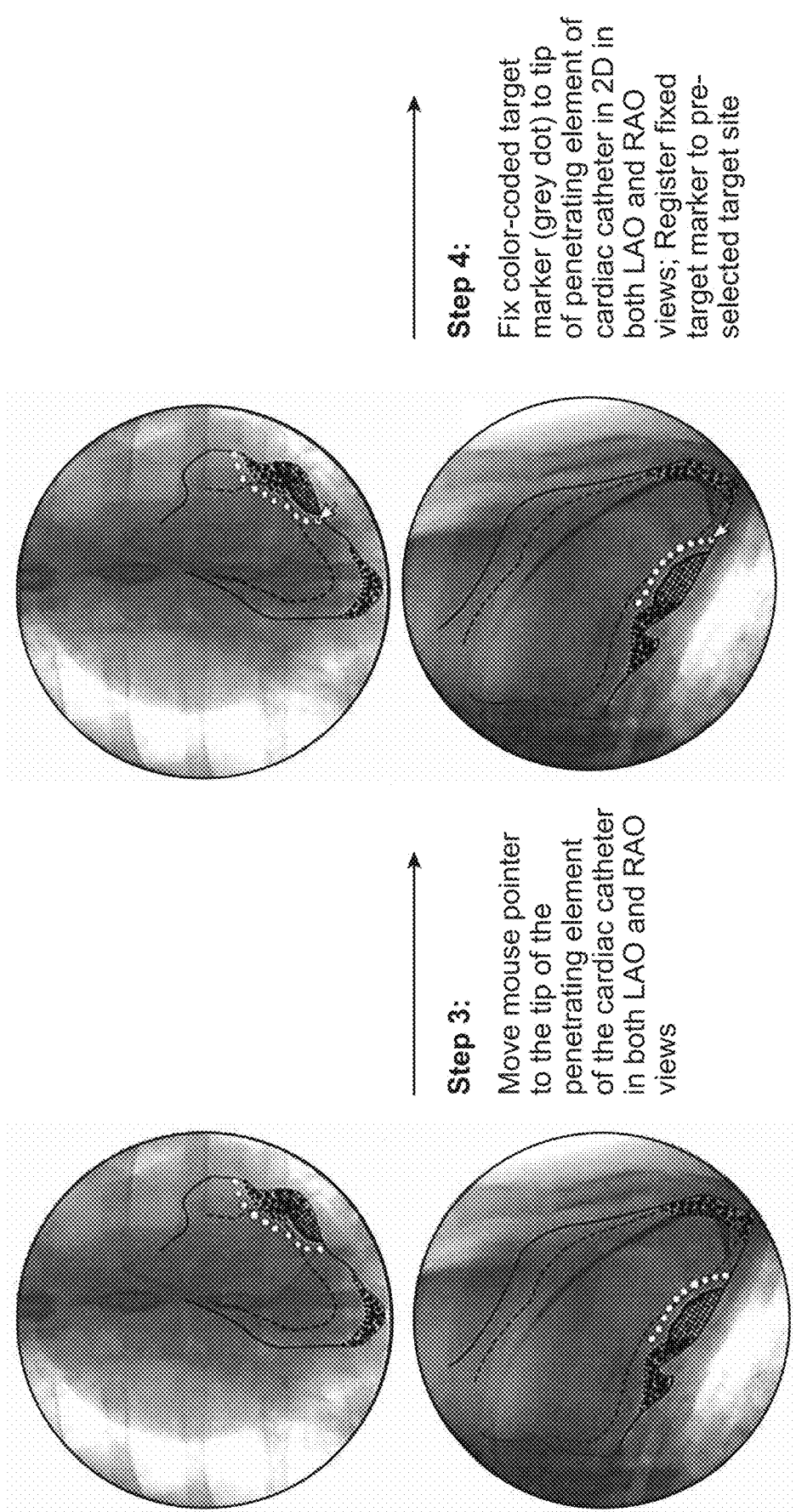
FIG. 2 (Cont. 1)

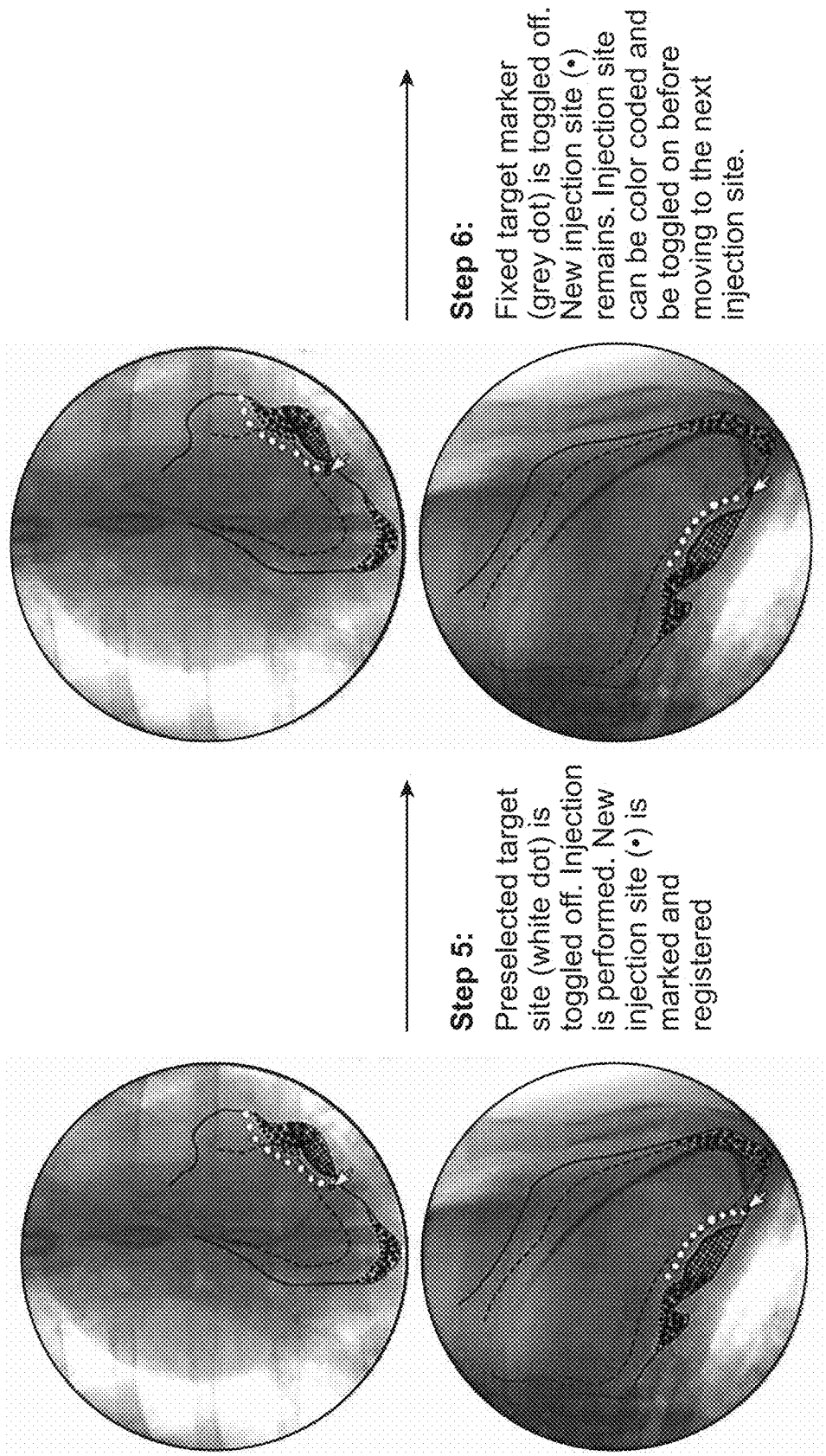
FIG. 2 (Cont. 2)

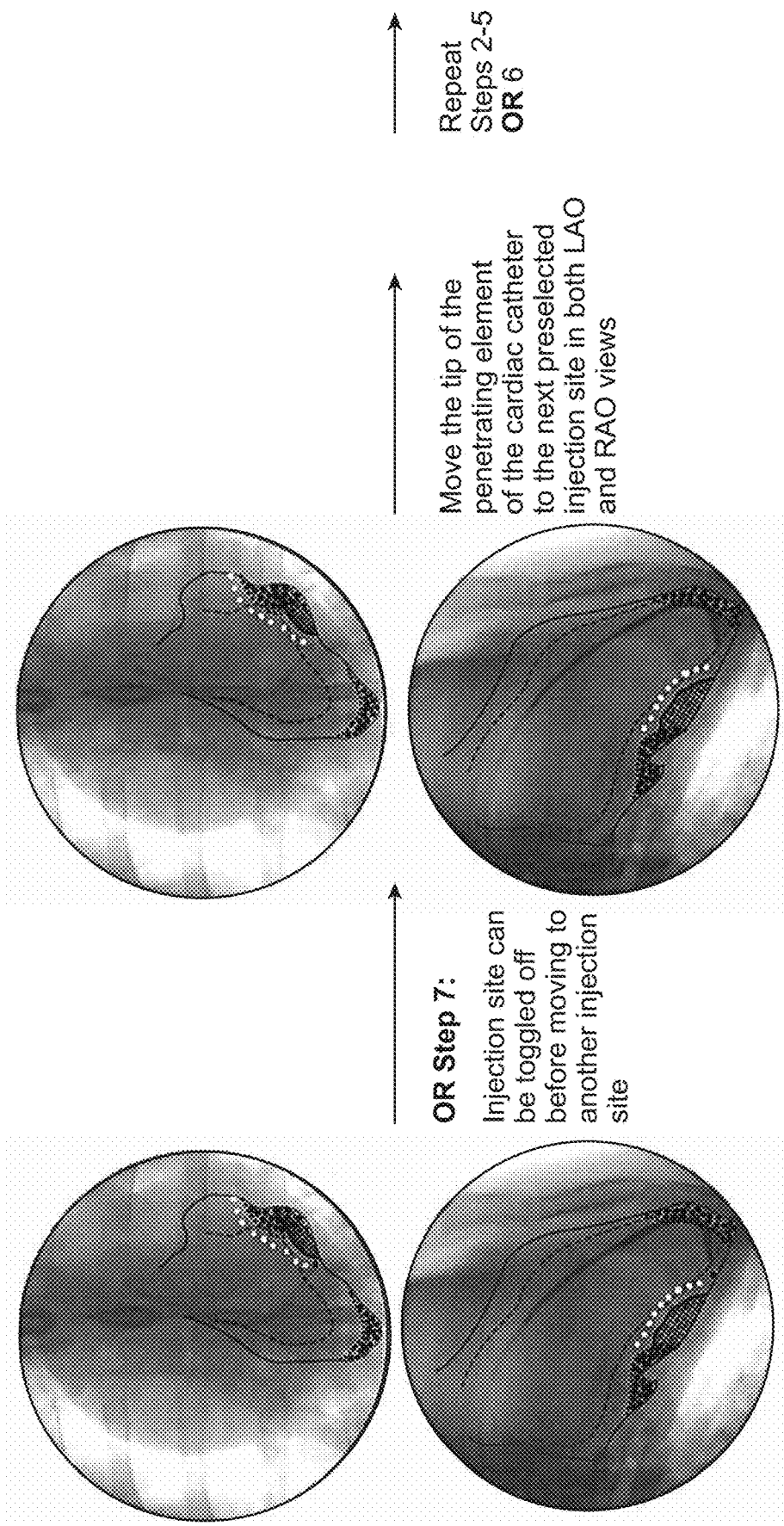
FIG. 2 (Cont. 3)

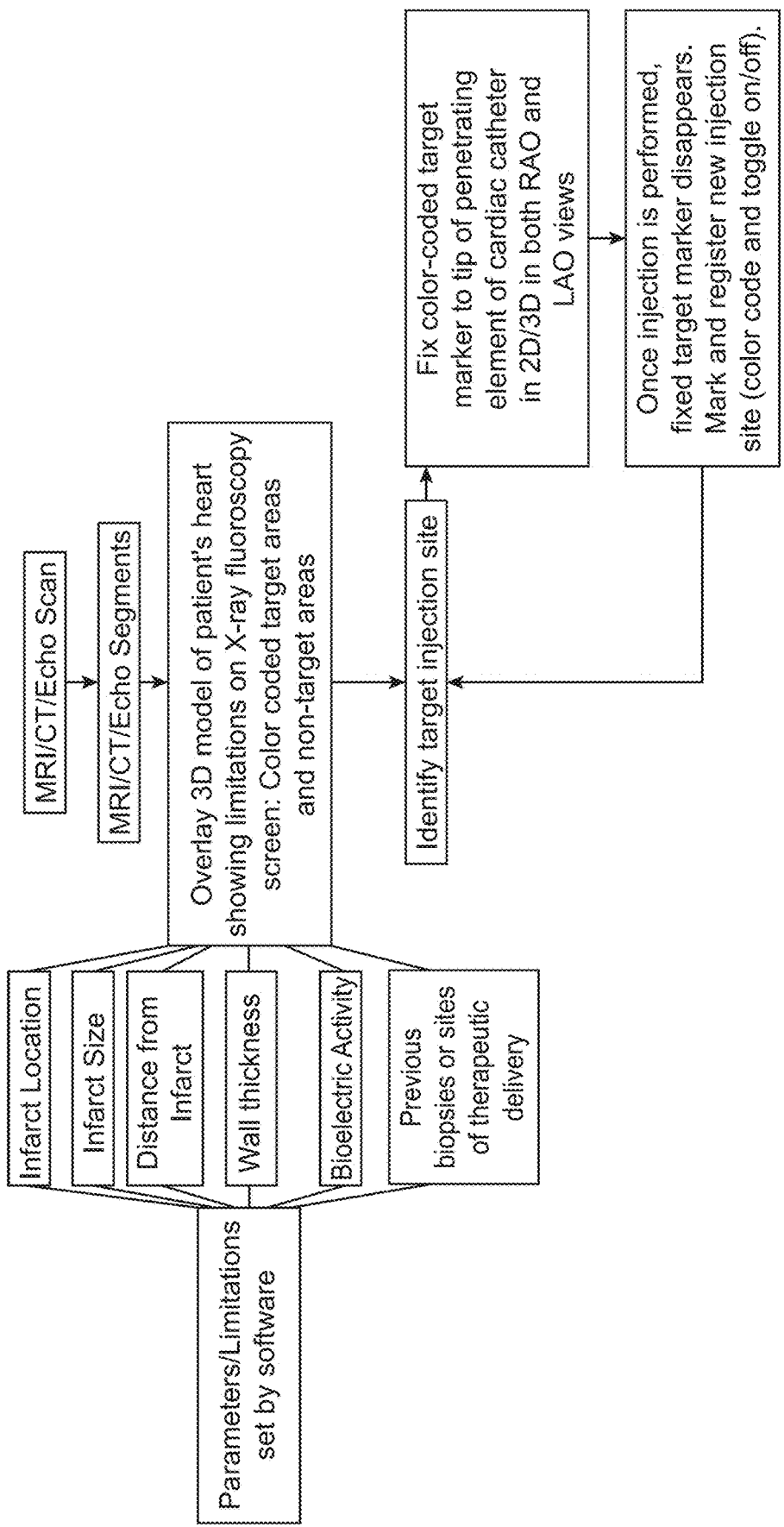

TARGET SITE SELECTION, ENTRY AND UPDATE WITH AUTOMATIC REMOTE IMAGE ANNOTATION

CROSS-REFERENCE TO RELATED APPLICATIONS

This Applications is a continuation of International Patent Application No. PCT/US2014/010732, filed Jan. 8, 2014, which claims priority to Provisional Application No. 61/750,226, filed Jan. 8, 2013; Provisional Application No. 61/750,233, filed Jan. 8, 2013; and Provisional Application No. 61/750,237, filed Jan. 8, 2013, the entire contents of which are incorporated herein by reference.

BACKGROUND

1. Field of the Invention

The present invention relates generally to imaging modalities and more particularly to methods and systems for fluoroscopic imaging of an anatomy and remotely annotating the image to show additional image or other information useful during surgery.

Imaging modalities, such as MRI, CT, and echocardiography, are used in cardiovascular diagnostic applications and may be fused to X-Ray fluoroscopy using custom software to register and overlay the MRI, CT or echocardiography-derived two-dimensional (2D) and three-dimensional (3D) images of a heart to display the endocardium, epicardium, infarct and other regions and/or data of interest onto a live X-ray fluoroscopy image.

Cardiovascular disease is a leading cause of death in industrialized nations and the number one cause of death in the United States. More than 7.9 million American adults have suffered a myocardial infarction (MI), with 1.1 million new or recurring MI cases each year. MI is characterized by restricted blood flow resulting in oxygen starvation and eventual large-scale loss of cardiac muscle, which cannot spontaneously regenerate, ultimately leading to heart failure. Current existing treatments for restoring heart function after myocardial injury are so far limited to a strict medication regimen and cardiac transplantation as a last resort. However, demand far exceeds supply of healthy donor hearts, leaving the cardiovascular community to strive towards novel promising therapeutic strategies including tissue engineering, gene therapy and cell therapy. Recent clinical trials have tested different types of stem cells, genes and growth factors using several delivery routes such as intramyocardial injection including both epicardial and transendocardial injections, intracoronary infusion, intravenous infusion and retrograde delivery. However, it has been shown that intramyocardial transendocardial injections while being minimally invasive, also have improved acute retention compared to the other delivery routes. This improved retention in transendocardial delivery leads to a strong potential for treatment for tissue regeneration and functional recovery and has been shown to slow down and eventually reverse adverse remodeling after a myocardial infarction. In recent MI patients, the infarct zone may be very fragile and intramyocardial injections in the infarct zone or the border zones of the infarct may have increased risks of perforation and pericardial effusion, which may lead to cardiac tamponade, a life threatening event. In these cases, accurate site targeting and injection of biotherapeutic agents is critical to the safety of the patient.

In conventional cardiovascular catheterization procedures, X-Ray fluoroscopy is typically used to assist the interventional cardiologist in guiding catheters such as a balloon catheter to the occluded artery in the heart during angioplasty; or in guiding catheters with a miniature grasping device at the end during cardiac biopsies; or in guiding a percutaneous injection catheter to and within the myocardium for transendocardial injections of biotherapeutic agents such as cells, genes, peptides, proteins (for example, growth factors and chemoattractants). Consequently, the catheters employed in cardiovascular catheterization procedures are designed to be X-ray visible so that they can be clearly seen and tracked during the procedure. However there are a few disadvantages of using only X-ray fluoroscopy for more complex procedures such as transendocardial injections and they can have significant impact on catheter guidance and image interpretation. (1) X-ray imaging is a projection imaging modality and typically two orthogonal views—Right Anterior Oblique (RAO) and Left Anterior Oblique (LAO)—are required to get an accurate sense of the location and orientation of the catheters in the heart in three-dimensional (3D) space. (2) Because two views are required, if the catheterization suite is equipped with a single plane X-ray fluoroscopy system, then the X-ray C-arm needs to be constantly rotated between these two views throughout the procedure to obtain the projections needed, thus allowing for proper guidance of the transendocardial catheters to selected intramyocardial target injection sites. This becomes unquestionably easier if the catheterization suite is equipped with a bi-plane X-ray fluoroscopy system. (3) While X-ray imaging provides excellent device visualization, it offers little insight in cardiac tissue visualization. X-ray fluoroscopy does not distinguish healthy tissue from infarct tissue or tissue in the infarct border zone region nor does it provide a 3D anatomical and topographical view of the patient's heart. This may be especially important to the interventional cardiologist who, depending on the therapy of choice, is attempting to accurately target healthy tissue, infarcted tissue, infarct border zone tissue, or a combination thereof, for intramyocardial injections of biotherapeutic agents. For these reasons, image fusion systems that can combine X-ray fluoroscopy with anatomical and functional 3D models reconstructed from magnetic resonance (MR) or computed tomography (CT) images, thereby providing real-time information and visualization of the catheters, are of particular interest for these applications.

Magnetic resonance imaging (MRI) is the most accurate diagnostic imaging modality which can provide a high-quality 3D anatomical and functional roadmap of a patient's heart and it is therefore most commonly used with X-ray fluoroscopy in these fusion imaging systems. Cardiac MRI segments from which cardiac images can be reconstructed are obtained with excellent tissue contrast. These cardiac images allow accurate and efficient differentiation between healthy tissue, infarcted tissue and infarct border zone tissue. However, most catheters and other cardiac devices, while safe to use and visualize with X-ray fluoroscopy, are not entirely compatible with MRI. Most of these devices contain ferromagnetic materials that can result in imaging artifacts as well as be a safety hazard to the patient exposed to a strong magnetic field during MRI. Further, even with the most sophisticated techniques and instruments available, capturing MRI images can still take between fifteen to sixty minutes depending on the types of images being acquired and the MRI sequence being run. Therefore, it makes sense that MRI scans are performed prior to the interventional procedures. Cardiac images reconstructed from these scanned segments can then be used concurrently with X-ray fluoroscopy to guide interventional cardiologists during transendocardial procedures to accurately and safely target regions of healthy, infarct and/or infarct border zone tissue, whether for injection of biotherapeutic agents or sampling of cardiac tissue.

2. Description of the Background Art

Methods and systems for fusing pre-operative images and information on real-time fluoroscopic images are described in U.S. Pat. No. 6,466,813; in U.S. Patent Publication Nos. 2008/0043901; 2011/0087088; and 2011/0087110; and in Tomkowiak et al. (2011) Catheterization and Cardiovascular Interventions 78:468-478. See also, U.S. Pat. No. 7,848,553 and U.S. Publication No. 2013/0102890.

SUMMARY OF THE INVENTION

The purpose of this invention is to facilitate the selection and the targeting of injection sites for biotherapeutic delivery or other injectables within the myocardium using transendocardial injection catheters, equipped with a penetrating element at the distal end of the catheters, in patients suffering from cardiovascular disease including but not limited to chronic myocardial ischemia, acute myocardial infarction; chronic heart failure comprising ischemic and nonischemic heart failure, and dilated cardiomyopathy. Biotherapeutics delivery includes cell therapies, gene therapies, protein and peptide therapeutics, and small molecule pharmaceuticals. Injectables delivery includes but is not limited to synthetic polymers, natural biopolymers, microparticles within the range of 15 to 150 μm. The present invention can also be used to select and target sampling sites for heart biopsy procedures testing for immune rejection in patients undergoing or having undergone a heart transplant; in patients showing signs of cardiomyopathy, cardiac amyloidosis and myocarditis; or in patients whose heart cells are being harvested for other therapeutic or diagnostic purposes.

Fluoroscopic imaging of a patient's heart is performed by positioning a patient in a sterile field and imaging the heart using an x-ray fluoroscopy system within the sterile to produce a two-dimensional image. The two-dimensional image is simultaneously displayed on an operative display within or adjacent the sterile field and on a display of a remote image processor outside the operative field. The two-dimensional image of the remote display is manually marked or annotated to show anatomical or treatment information which is simultaneously shown on the operative display.

Manually marking the image may comprise manipulating a graphical user interface on the remote image processor, and the graphical user interface comprises a touchscreen, a mouse, a roller ball, or a joy stick. Manually marking the two-dimensional image may comprise marking any one or more of an outline of the heart or portions thereof, target treatment regions, regions to avoid treating, and the like.

In a second aspect of the present invention, a patient's heart is imaged using a catheter to produce a real time image. The image is presented on a screen and sent to an image processor. Treatment parameters are input to the image processor, and the image processor calculates locations of a plurality of target treatment sites which are displayed on the screen. The catheter is advanced to position a treatment element on the catheter proximate a location of a target treatment site, where the actual position of the treatment element may differ from calculated location. After treating at the actual treatment position, an image processor calculates a difference between the positions of the calculated and actual treatment sites. The locations of all remaining target treatment may be recalculated by the image processor.

Imaging may comprise producing a two-dimensional image using x-ray fluoroscopy or producing two orthogonal two-dimensional images. Imaging may further comprise superimposing on the two-dimensional image an outline of the heart, where superimposing may comprise providing a static three-dimensional image of the heart, where the image processor registers the three-dimensional image with the two dimensional image and calculates the outline which is projected on the two dimensional image. Alternatively, superimposing may comprise manually entering the outline which is projected on the two dimensional image. The methods of the present invention may further comprise repeating the advancing, determining, treating and recalculating steps for successive treatment sites.

In a third aspect, the present invention facilitates the selection and the targeting of injection sites for biotherapeutic delivery or other injectables within the myocardium using transendocardial injection catheters, equipped with a penetrating element at the distal end of the catheters, in patients suffering from cardiovascular disease including but not limited to chronic myocardial ischemia, acute myocardial infarction; chronic heart failure comprising ischemic and nonischemic heart failure, and dilated cardiomyopathy. Biotherapeutics delivery includes cell therapies, gene therapies, protein and peptide therapeutics, and small molecule pharmaceuticals. Injectables delivery includes but is not limited to synthetic polymers, natural biopolymers, microparticles within the range of 15 to 150 μm. The present invention can also be used to select and target sampling sites for heart biopsy procedures testing for immune rejection in patients undergoing or having undergone a heart transplant; in patients showing signs of cardiomyopathy, cardiac amyloidosis and myocarditis; or in patients whose heart cells are being harvested for other therapeutic or diagnostic purposes.

A patient's heart is imaged using a catheter to produce a real time image which is displayed on a screen. The image is also sent to an image processor where treatment parameters are input. The image processor then calculates safe regions and/or unsafe regions for performing a treatment or diagnosis within the heart based upon the inputted treatment conditions. The image processor superimposes information on the image on the screen to identify the safe and/or unsafe regions. The superimposed information may comprise at least one of color coding, creation of boundaries, insertion of written information, and insertion of icons.

The invention has other advantages and features which will be more readily apparent from the following detailed description of the invention and the appended claims, when taken in conjunction with the accompany drawings.

BRIEF DESCRIPTION OF THE DRAWINGS

FIGS. 1-5 illustrate the specific examples described below.

DETAILED DESCRIPTION

Figure 2:
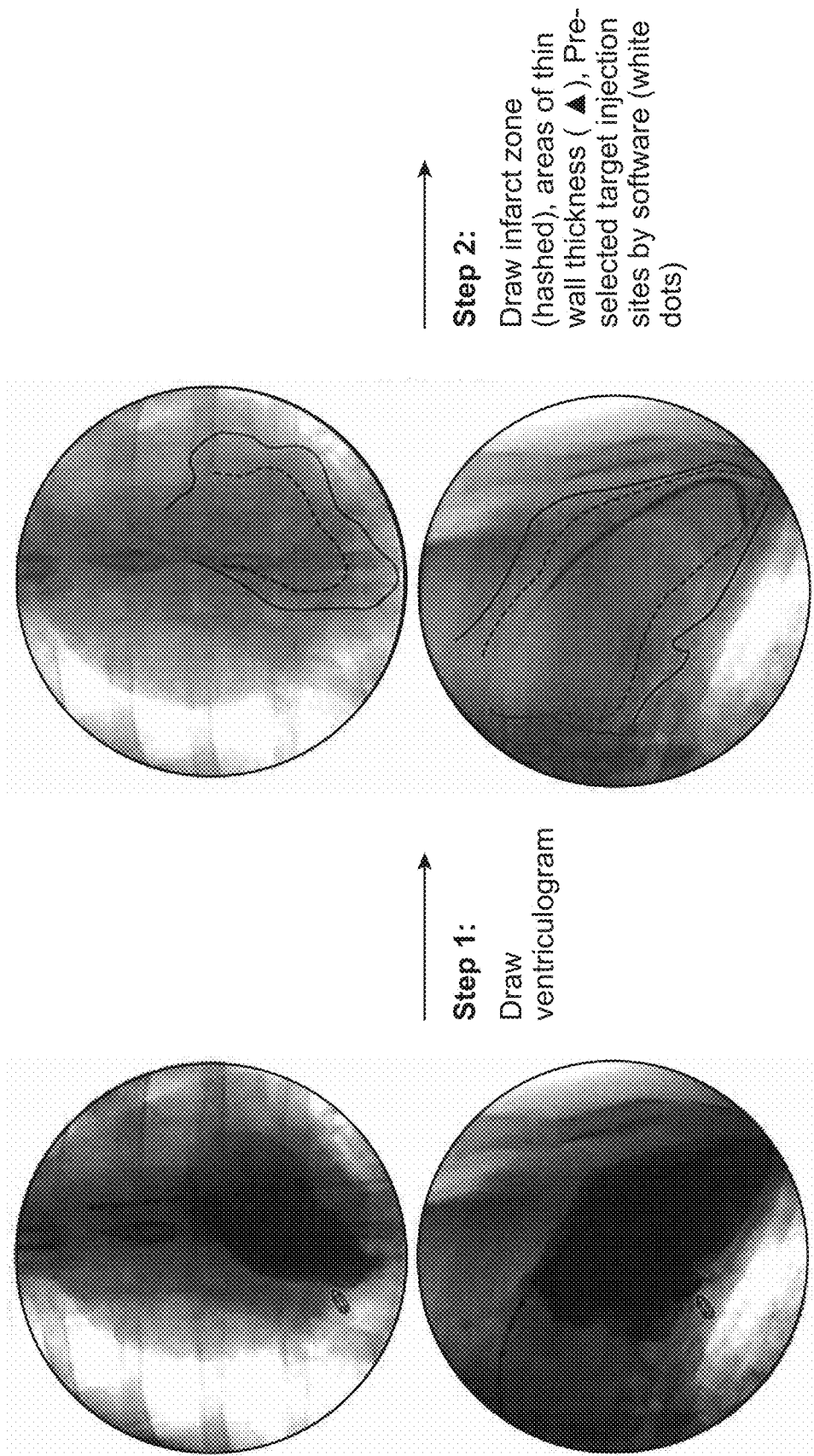

In this invention we combine a 3D model reconstruction of the heart derived from magnetic resonance imaging performed prior to an interventional procedure with live X-ray fluoroscopy images during a catheterization procedure to facilitate catheter guidance within the myocardium and therefore, improve the safety and accuracy of transcatheter injections of biological and chemical therapeutic agents in the diseased heart. Cardiac MRI slices, detailing the endocardial and epicardial surfaces of the heart and the infarct regions in the heart, are acquired during MRI scans.

Commercially available platform-independent contouring packages or other freeware such as Segment (Medviso), The Visualization Toolkit (Kitware, Inc.), QMass® MR Enterprise Solution (Medis medical imaging systems, Inc.), are used to define the endocardial and epicardial walls and the infarct for each slice and thus, generate a 3D model of the patient's heart prospectively to the interventional procedure. It should be noted that any other imaging modality (for example, CT, echocardiography) that can define the anatomical and functional details of the heart and from which a 3D model can be reconstructed, can alternatively be used in place of MRI. The only criterion is the output format from the contouring packages which needs to conform to the X-ray fluoroscopy system. Prior to the procedure, the 3D space within the field of view of the fluoroscopy system is virtually created within the fusion imaging system. During the interventional procedure, a ventriculogram is taken of the patient's left ventricle in two orthogonal views. The 3D model created from the MRI scan is then virtually placed into a 3D space and registered to fit the ventriculograms of the X-ray fluoroscopy system. The 3D model is thus transposed either in 2D or 3D onto the live X-ray fluoroscopy screen. The software of the fusion imaging system can then be used to define and display essential parameters and limitations central to the safe treatment of the patient according to the study protocol. For example, in the case of transendocardial intramyocardial injections of biotherapeutic agents into the patient's heart, important information such as the myocardial infarct location and size, differentiation between infarct zones if there is more than one, left ventricular wall thickness, hypokinetic and akinetic regions, target injection zones and 'Do not inject' zones (including but not limited to the papillary muscle, regions close to the mitral valve, the apex, the basal septal wall where the HIS bundle lies and thin regions of the myocardial wall) are necessary data points for the safe treatment of the patient. These data points can be obtained from MRI segments or CT slices and using the software interface, can thus be translated within the 2D or 3D model of the heart prior to the interventional procedure, thereby creating an anatomical and functional roadmap of the heart. Based on the inclusion and exclusion criteria for intramyocardial injections in each study, specific regions will be traced and demarcated using different colours and/or patterns, thus clearly displaying the selected target regions of interest and the 'Do not inject' zones to the interventional cardiologist.

Here we disclose specific embodiments for fusion imaging systems with X-ray fluoroscopy, cardiac catheters, transendocardial injection catheters, and methods of use to register and transpose multi-modality images to guide targeted procedures within the myocardium such as transendocardial deliveries and cardiac biopsies.

Recording of left ventricle contours and target sites on screen—2D

Example 1

As previously discussed, one of the major disadvantages of using only X-ray fluoroscopy in cardiac intervention procedures is that X-ray fluoroscopy is a projection imaging modality and it typically requires projections in two orthogonal views—RAO view and LAO view—to determine the location and orientation of the percutaneous catheters in the left ventricle. During a typical transendocardial injection procedure in a catheterization suite equipped with a single plane X-ray fluoroscopy system, two transparencies are overlaid and secured onto the single monitor of the X-ray system. At the start of the procedure, a ventriculogram is performed during which contrast dye is injected into the left ventricle and the left ventricle is mapped. During mapping, the left ventricular contours of the heart in diastole and systole are traced on one transparency in one orthogonal view; that transparency is then flipped out of the way; the C-arm of the X-ray fluorosocopy system is rotated to switch to the other orthogonal view; and the contours of the heart in diastole and systole are traced in that view on the second transparency. The transendocardial injections are then performed and each time an injection is made, the injection site is also marked in both orthogonal views on the two transparencies. This requires constant switching between the orthogonal views and between the transparencies. Depending on the number of injections, this back and forth switching of the transparencies in each view and of the C-arm of the X-ray fluoroscopy system is performed numerous times during a single procedure and can become cumbersome while increasing the length of the procedure. Further, the person changing the overlays stands close to the sterile zone and should be careful not to accidentally break sterility. That person also usually stands close to the C-arm of the X-ray fluoroscopy system and can therefore be inadvertently exposed to a significant dose of X-rays.

In one embodiment of this invention, as shown in FIG. 1, we eliminate the use of transparencies. Using the ventriculogram, the left ventricular contours of the patient's heart in diastole and systole are digitally outlined with a touchscreen, mouse, tablet or other graphical input device and displayed on a monitor of a separate computer or work station in both orthogonal views in 2D space either in the control room or in a designated area of the catheterization suite away from the X-ray fluoroscopy system and outside of the sterile zone. The computer or work station has an internal modem or network connection device which is in communication with the computer of the single plane X-ray fluoroscopy system via an intranet communications link system. The communications link to the network may be of any acceptable type, including telephone lines, fiber optics, cable modem links, wireless data transfer systems among others. What is thus input and displayed on the monitor of the separate computer or work station is output onto the monitor of the single plane X-ray fluorosocopy system and vice versa. For transendocardial injections of biotherapeutic agents into the patient's hearts, information such as the myocardial infarct location, hypokinetic and akinetic regions, and 'Do not inject' zones as previously described are important to identify. This information may be displayed on a monitor in the catheterization suite and will help guide the interventional cardiologist during the procedures. This is done after mapping the left ventricle in the two orthogonal views and prior to the start of the transendocardial injection procedures. Based on the specific requirements of the procedure and the therapy, the operator marks these important zones on the remote computer to clearly define the areas where injections should and should not be made on the ventriculograms in both orthogonal views. These demarcations are done by color coding, by the use of solid and dashed lines, and/or by the use of different shapes and patterns. As previously stated, the two orthogonal views are helpful to verify the location and orientation of the percutaneous catheters in the left ventricle and to verify and mark an injection site. A function or key is used to toggle between the annotated LV contour maps in the two orthogonal views on the remote computer and displayed on the monitor of the X-ray fluoroscopy system. Toggling between the two LV contour maps enables the operator to remotely mark up the target injection sites in each view without having to switch between transparencies secured to the monitor of the single plane X-ray fluoroscopy system in the catheterization suite. Marking of the injection sites is done by digitally marking the location of the catheter tip during the transendocardial injection process. If it is isocentered and the table is not moved, a single label should be valid in both views. Marks may be color coded, have varying shapes or sizes and/or have any number of associated fields to record additional information. The site coloring or numbering can be subsequently displayed with adjustable level of transparency or hidden on the display. They may be grouped such that certain properties may be changed for the group instead of individually. A number of parameters associated with the marked sites may further be displayed on the screen in a separate window. In the latter, the operator is able to choose the parameters he or she wants to appear next to the marked injection site if needed by checking or unchecking checkboxes associated with such parameters. Examples of these parameters include the injection site number, the total number of injections, the volume of therapeutic agent injected (ranging from 0.1 ml to 1.0 ml per injection for intramyocardial injections), the dosage of therapeutic agent being delivered (concentration, total number of cells ranging from $1.\times.10^6$ to $200.\times.10^6$, total amount of plasmid/gene or peptide or protein, total number of particles), a time stamp, screen coordinates, the ventricular wall thickness or electrophysiologic activity at that injection site, the segment injected based on a 17-segment bull's-eye map, its distance from the infarct location, its distance from other injection sites.

If a bi-plane X-ray fluoroscopy system is available in the catheterization suite, the same capabilities of the software will be available. However, there is no need to toggle from RAO view to LAO view since both views are typically projected onto two separate screens mounted to the bi-plane X-ray system. In this case, the two projected fluoroscopic images are independently input into the computer and subsequently output with the associated annotations as described above to either two independent displays or as two windows on a single display.

The software interface will also enable the 2D left ventricle image projections, the marked injection sites and the parameters in either view to be toggled ON and OFF.

Example 2

Preselected Target Sites

In this example, as shown in FIG. 2, we describe a second method for selecting target points within the heart of a patient for injecting therapeutic agents in transendocardial intramyocardial interventions or for sampling tissue in biopsy procedures. In this method, the same procedure as in Example 1 is followed but the target sites are preselected either manually or using various algorithms. These algorithms may be executed by a computer and may result in (1) a uniform equally distributed grid projection on the endocardial surface; (2) a uniform grid excluding the infarct zone and spaced at 0 to 20 millimeters from the infarct zone; (3) a uniform grid within the infarct zone; (4) a uniform grid distally located and equally distributed within the distal third of the ventricle or the apical region of the left ventricle; (5) a uniformly distributed circular pattern or other functional geometric distributions that may be preferred. The target sites ranging in number from 1 to 20 are thus preselected based on a set of parameters required for the specific procedure. In addition to what is described in Example 1, these parameters can further include distance from the infarct zone, wall thickness of at least 5 millimeters, distance between injection sites (greater or equal to 5 millimeters), equally spaced injection sites, randomly spaced injection sites from the infarct zone, randomly spaced injection sites at a defined distance from the infract zone and can exclude previous sites of therapeutic delivery for transendocardial injections and previous sampling sites for cardiac biopsies. Before the day of the procedure, diagnostic cardiac MRI scans, CT scans and echocardiography may be used to determine required pre-specified information which includes but is not limited to wall thickness and infarcted tissue location. On the day of the procedure, prior to the start of the procedure, a ventriculogram is performed in both orthogonal views and the contours of the left ventricle mapped as described in Example 1. An algorithm selected from the list described above is then executed by the computer and target sites are pre-selected with the pre-defined parameters and are then displayed. Similar to Example 1, display of the preselected target points is done by means of markers of different shapes, patterns and/or colours which can be toggled on and off, grouped or ungrouped. The tip of the penetrating element at the distal end of the transendocardial catheter or the guiding biopsy catheter is then moved to one of the preselected target points. Once the injection or sampling has been performed, the actual injection site is then marked at which point the preselected target point may be hidden or replaced. The marker for the actual injection or sampling marker may be of different shape, pattern and/or color than the target marker(s). The new marker is saved and may be shaded or hidden before moving to the next preselected target point. If the actual target site differs from the preselected target site, an algorithm can be applied to readjust the rest of the preselected target sites based on the parameters forced on the pre-selection. This algorithm can be rerun after each injection/sampling is performed to adjust the preselected sites accordingly. Further, if the interventional cardiologist is not satisfied with the preselected target sites, the interventional cardiologist can indicate where he/she prefers the first site to be and that site can be registered by clicking on the new site position in both RAO and LAO views and the algorithm can then be rerun to change the locations of the rest of the preselected target sites relative to the redefined first site.

Actual target sites within the left ventricle of a patient, where injection has been performed, are registered and saved. These target points can be displayed along with a series of parameters comprising the patient identification number, an injection number, a time stamp, the identity of the therapy injected, the volume injected at the injection site, the concentration injected, the total dosage injected, screen coordinates, the wall thickness and/or electrophysiologic activity at the injection sites, the distance from the infarct location to the injection sites, the distance from the nearest injection site, and the quality or character of contrast delivery from either the base of the penetrating element or through the distal penetrating element. In the case where sampling is performed, such as in right ventricular cardiac biopsy, the series of parameters can include the previous record of where samples have been taken from a patient's heart including data related to the sample character such as their rejection grade score. This may facilitate future sampling strategy and algorithm pre-selection as discussed in example 2. Additional parameters include patient identification number, a sample number, a time stamp, a set of coordinates where the tissue is being sampled, the wall where the sample is taken, the segment of a standard 17-segment heart model bulls-eye plot where the sample is taken, the wall thickness at the sampling site, the distance of the sampling site from the infarct location, and the distance from the nearest sampling site if more than one sample is taken. With a sampling device or bioptome that includes the ability to deliver contrast either through a penetrating distal element in the tissue or a contrast port at the base of the biopsy element, the quality or character of contrast delivered through the catheter from either the base of the penetrating element or through a penetrating element could also be recorded. Similarly with a sampling device that enables the recording of bipolar signals, the electrophysiologic activity at the sample site could also be recorded, Recording of target sites on screen—3D

Example 3

Here, as shown in FIG. 3, we describe a method for selecting target points within the left ventricle of a patient to inject therapeutic agents in transendocardial intramyocardial interventions or to sample tissue in biopsy procedures. In this method, we combine a 3D heart model reconstructed prior to an interventional procedure from cardiac slices obtained using an imaging modality capable of 3D visualization of cardiovascular structures (magnetic resonance imaging, computer tomography, echocardiography), with live X-ray fluoroscopy images during a catheterization procedure. After acquisition of the patient's ventriculogram, the 3D model reconstruction of the heart is registered onto the orthogonal ventriculograms, and projected onto the live X-ray fluoroscopy images. This creates combined X-ray projection images with an overlay of the registered MR, CT or echocardiography images.

Registration is achieved by first aligning at least two anatomical fiducial markers on the 3D reconstructed model with corresponding points on the ventriculograms in the two orthogonal views. This and all subsequent steps in target point selection are performed on a separate computer or workstation in the control room or in a designated area of the catheterization suite away from the X-ray fluoroscopy system and the sterile zone and in direct communication with the X-ray fluoroscopy system such that the resulting output can be displayed on the monitor of the fluoroscopy system or to separate monitors visible to the physician. Target injection or sampling areas are selected based on the inclusion and exclusion criteria of the procedures. For instance, for transendocardial intramyocardial injections, wall thickness less or equal to 5 millimeters, the location of the infarct, the size of the infarct, the distance from the infarct to the injection site and the basal section of the septal wall of the left ventricle can be identified and marked along the 3D surface of the left ventricle on the remote computer and output onto the fluoroscopy monitor. Similarly, in the case of tissue sampling for biopsy procedures, the wall thickness, the location of the infarct, the size of the infarct and previous biopsy sampling sites can all be marked. These areas may be denoted by colour coding, by the use of solid and dashed lines, and/or by the use of different shapes and patterns. These demarcations allow the interventional cardiologist to view where he/she should or should not inject therapies or sample tissue. During the procedure, the tip of the penetrating element at the distal end of the transendocardial injection catheter or of the guiding biopsy catheter is moved to a target point. Using visual recognition, the target point is fixed in 2D space by means of a target marker on the monitor. The target marker is overlapped onto the tip of the penetrating element in two orthogonal RAO and LAO views, wherein the target marker can be forced to travel in 3D space along the endocardium when it is in target identification mode so that it is in the same 3D space as the tip of the penetrating element. Registration of the fixed target point and the target marker is done by means of markers which can take different shapes, and can be colour coded. When the injection or sampling has been performed, registration of the actual injection point is done by replacing the target point marker with a marker having a different shape and/or colour. The new marker is saved and can be hidden or shaded before moving to the next target point.

As in Example 1, if a bi-plane X-ray fluoroscopy system is available in the catheterization suite, there is no need to toggle from RAO view to LAO view since both views are typically projected onto two separate screens mounted to the bi-plane X-ray system.

Example 4

Figure 4:
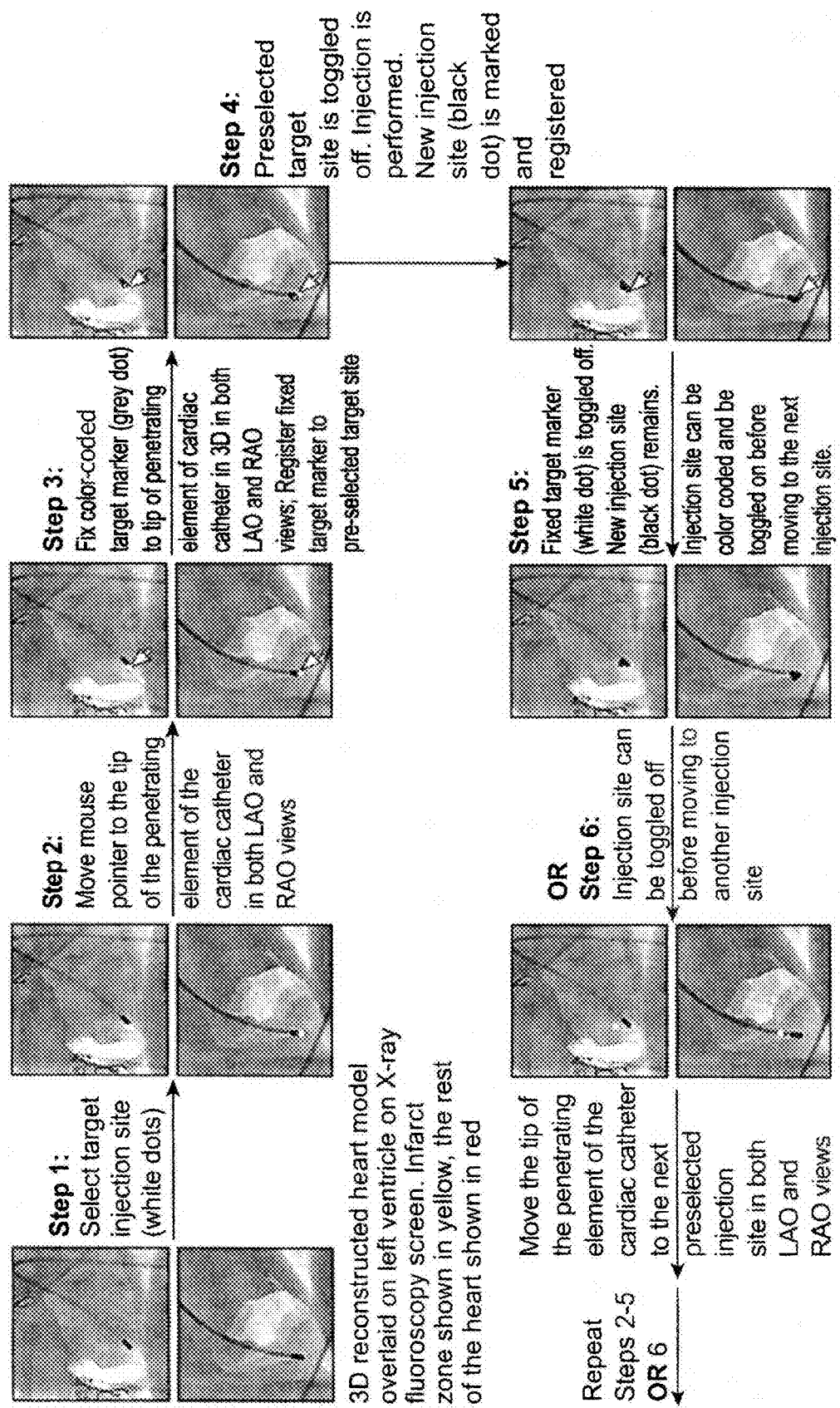

In another embodiment, as shown in FIG. 4, we describe a method of fitting a 2D heart model onto left ventriculograms in both RAO and LAO views and subsequently, onto live X-ray fluoroscopy images. The same steps are followed and the same software capabilities are used as in Example 2. However, instead of fitting a 3D model of the left ventricular contours, data obtained from cardiac MRI, CT or echocardiography segments are used to reconstruct a 2D model of the left ventricle in the same plane as the fluoroscopic projection prior to the procedure, and the same regions of interest and parameters as detailed above are marked onto the 2D model. These markings are done primarily through colour coding, the use of solid and dashed lines, and/or by the use of different shapes and patterns, which can be toggled on and off. Otherwise, the selection and registration of the target sites are performed in the same way as described in Examples 1 and 2.

As in Examples 1 and 2, if a bi-plane X-ray fluoroscopy system is available in the catheterization suite, the need to toggle from RAO view to LAO view is thereby eliminated since both views are typically projected onto two separate screens mounted to the bi-plane X-ray system.

Example 5

Figure 5:
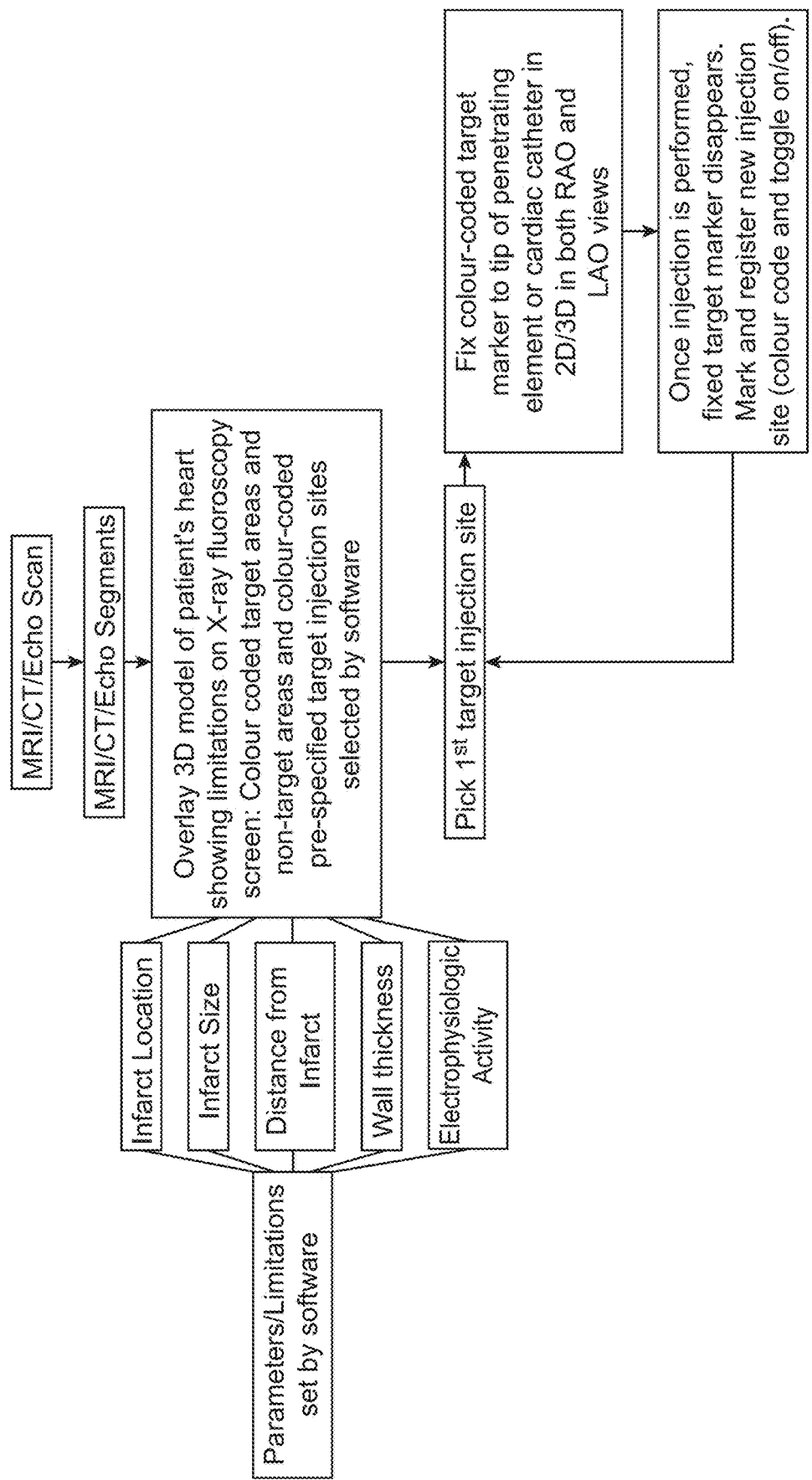

In this example, as shown in FIG. 5, we describe a second method for selecting target points within the left ventricle of a patient for injecting therapeutic agents in transendocardial intramyocardial interventions or for sampling tissue in biopsy procedures with the help of multi-modal fusion imaging. In this method, the same procedure as in Example 3 is followed with the difference that the target sites are preselected using a computer algorithm. The computer algorithm is programmed to choose the target sites ranging in number from 1 to 20 based on a set of parameters required for the specific procedure. In addition to what was previously described in Example 3, these parameters can include distance from the infarct zone, distance between injection sites (greater or equal to 5 millimeters), equally spaced injection sites, randomly spaced injection sites from the infarct zone, randomly spaced injection sites at a defined distance from the infract zone, or pre-specified electrophysiologic activity. Prior to the start of the procedure, the target sites are preselected using the algorithm with the pre-defined parameters and they are displayed by the software. Similar to Example 3, display of the preselected target points is done by means of markers of different shapes, patterns and/or colors which can be toggled on and off. The tip of the penetrating element at the distal end of the transendocardial catheter or the guiding biopsy catheter is then moved to one of the preselected target points. Once the injection or sampling has been performed, the actual target point is then registered by replacing the marker marking the preselected target point with a new marker of different shape, pattern and/or colour. The new marker is saved and can be shaded or hidden before moving to the next preselected target point. If the actual target site differs from the preselected target site, an algorithm can be applied to readjust the rest of the preselected target sites based on the parameters forced on the pre-selection. This algorithm can be rerun after each injection/sampling is performed to adjust the preselected sites accordingly. Further, if the interventional cardiologist is not satisfied with the preselected target sites, the interventional cardiologist can indicate where he/she prefers any target to be and that target can be registered by clicking on the new position in both RAO and LAO views and the algorithm can then be rerun to change the locations of the rest of the preselected target sites relative to the first.

In these examples, target points within the left ventricle of a patient, where injection has been performed, are registered and saved. These target points can be displayed with a series of parameters comprising of the patient identification number, an injection number, a time stamp, the identity of the therapy injected, the volume injected at the injection site, the concentration injected, the total dosage injected, screen coordinates, the wall thickness at the injection sites, electrophysiologic activity, the distance from the infarct location to the injection sites and the distance from the nearest injection site. In the case where sampling is performed, the series of parameters can include the patient identification number, a sample number, a time stamp, a set of coordinates where the tissue is being sampled, the wall where the sample is taken, the segment of a standard 17-segment heart model bulls-eye plot where the sample is taken, the wall thickness at the sampling site, electrophysiologic activity, the distance of the sampling site from the infarct location, the distance from the nearest sampling site if more than one sample is taken.

While the above is a complete description of the preferred embodiments of the invention, various alternatives, modifications, and equivalents may be used. Therefore, the above description should not be taken as limiting the scope of the invention, which is defined by the appended claims.

What is claimed is:

1. A method for fluoroscopic imaging of a patient's heart, said method comprising:
    using an imaging modality capable of three-dimensional (3D) visualization to obtain a 3D image of the patient's heart;
    imaging the heart using an x-ray fluoroscopy system in a sterile operative field to produce two orthogonal two-dimensional images, wherein the patient is positioned in the sterile operative field to image the heart;
    simultaneously displaying the two-dimensional images on both an operative display within or adjacent the sterile operative field and on a remote display of an image processor outside the sterile operative field;
    superimposing at least a portion of the 3D image of the patient's heart on the two-dimensional images on the remote display;
    marking the superimposed image to show anatomical information including wall thickness and at least one myocardial infarct location of the patient's heart;
    marking the superimposed image of the remote display to show treatment information, wherein marking the superimposed image comprises marking target treatment regions of the patient's heart suitable for delivery of a biotherapeutic; and
    simultaneously displaying, on both the operative display and the remote display, the marked superimposed image showing both the anatomical information and the treatment information, and
    wherein the biotherapeutic is delivered to one or more of the target treatment regions to treat said one or more of the target treatment regions.

2. The method of claim 1, wherein marking the superimposed image to show the anatomical information or the treatment information comprises manipulating a graphical user interface on the remote display.

3. The method of claim 2, wherein manipulating the graphical user interface comprises manipulating a touchscreen, a mouse, a roller ball, or a joy stick.

4. The method of claim 1, wherein marking the superimposed image to show anatomical information further comprises marking a region selected from the group consisting of a hypokinetic region, an akinetic region, a papillary muscle, a mitral valve, an apical segment of the heart, and a bundle of His.

5. The method of claim 1, wherein the three-dimensional image of the heart is selected from the group consisting of magnetic resonance imaging (MM), computed tomography (CT), and echocardiography-derived images of the heart.

6. The method of claim 1, wherein the two-dimensional images and the three-dimensional image are provided from different imaging modalities.

7. The method of claim 1, wherein the biotherapeutic is delivered to said one or more of the target treatment regions by injecting the biotherapeutic into said one or more of the target treatment regions.

8. The method of claim 1, wherein the biotherapeutic comprises one or more of a cell therapy, a gene therapy, or a protein and peptide therapeutic.

9. The method of claim 7, wherein injecting the biotherapeutic into said one or more of the target treatment regions comprises injecting one or more of a synthetic polymer, a natural biopolymer, or a microparticle into said one or more of the target treatment regions.

10. The method of claim 1, wherein the biotherapeutic is delivered transendocardially.

11. The method of claim 1, further comprising inputting one or more treatment parameters, calculating one or more locations of the target treatment regions, and simultaneously displaying the one or more locations of the target treatment regions on the marked superimposed image of the heart displayed on both the operative and remote displays.

12. The method of claim 11, further comprising advancing a treatment catheter proximate a location of one of the target treatment regions.

13. The method of claim 12, wherein the treatment catheter comprises a transendocardial catheter.

14. The method of claim 1, wherein the imaging modality capable of 3D visualization is selected from the group consisting of magnetic resonance imaging (MM), computed tomography (CT), and echocardiography.

15. The method of claim 1, wherein the 3D image of the patient's heart is obtained before the patient is positioned in the sterile operative field.

16. The method of claim 1, wherein marking the superimposed image to show the anatomical information comprises marking an outline of the heart or portions thereof.

17. The method of claim 1, wherein marking the superimposed image to show the anatomical information or marking the superimposed image to show the treatment information comprises marking regions of the patient's heart to avoid treating, wherein the regions to avoid treating comprise one or more a thin region of a myocardial wall, a papillary muscle, a region of the heart where treatment would affect a cardiac valve, an apical segment the heart, or a region of the septum of the heart.

18. The method of claim 1, wherein marking the superimposed image to show the anatomical information or marking the superimposed image to show the treatment information comprises marking regions of the patient's heart to avoid treating, and wherein the regions to avoid treating comprise one or more of a previously treated location or myocardial tissue which is not infarcted.

19. The method of claim 1, wherein the two orthogonal two-dimensional images comprise two orthogonal ventriculogram images.

20. The method of claim 19, wherein the two orthogonal ventriculogram images comprises a first ventriculogram image with a right anterior oblique view of the heart and a second ventriculogram image with a left anterior oblique view o the heart.

21. The method of claim 19, further comprising injecting dye into the patient's heart and taking at least two x-ray fluoroscopic images of the heart to generate the two orthogonal ventriculogram images.

\* \* \* \* \*